US00PP35155P2

(12) United States Plant Patent
Bedard

(10) Patent No.: US PP35,155 P2
(45) Date of Patent: May 9, 2023

(54) FLORIBUNDA ROSE PLANT NAMED 'WEKPIFLASPAS'

(50) Latin Name: *Rosa hybrida*
Varietal Denomination: WEKpiflaspas

(71) Applicant: Early Morning LLC, Lawrenceburg, IN (US)

(72) Inventor: Christian Bedard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/803,802

(22) Filed: Nov. 29, 2022

(51) Int. Cl.
*A01H 5/02* (2018.01)
*A01H 6/74* (2018.01)

(52) U.S. Cl.
USPC ..... Plt./145

(58) Field of Classification Search
USPC ..... Plt./145
CPC ... A01H 5/02; A01H 5/00; A01H 6/74; A01H 6/749
See application file for complete search history.

(56) References Cited

U.S. PATENT DOCUMENTS

PP18,473 P2 * 2/2008 Carruth ..... A01H 5/02 Plt./145
PP22,764 P3 6/2012 Meilland
PP24,726 P3 8/2014 Bedard

* cited by examiner

*Primary Examiner* — June Hwu
(74) *Attorney, Agent, or Firm* — McKee, Voorhees & Sease, PLC

(57) ABSTRACT

A new variety of Floribunda rose suitable for garden decoration, having flowers of soft gold coloration.

1 Drawing Sheet

Classification: The present disclosure relates to a new *Rosa hybrida* plant.

Variety denomination: The new plant has the varietal denomination 'WEKpiflaspas'.

BACKGROUND OF THE INVENTION

This invention relates to a new and distinct variety of Floribunda Rose. It has as its seed parent the variety known as 'MEIkolyma' (U.S. Plant Pat. No. 22,764) and as its pollen parent the variety known as 'WEKjunjuc' (U.S. Plant Pat. No. 24,726). It was hybridized by the Inventor.

SUMMARY OF THE INVENTION

Among the features which distinguish the new variety from other presently available and commercial rose cultivars known to the Applicant are the following combinations of characteristics: its many hairs on the bud surface, its heavily red suffusion all around the peduncle, its excellent color stability throughout the life of the flower and its rough under side of the rachis with few small prickles. The plant has a bushy upright somewhat spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKpiflaspas' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'MEIkolyma' by the following combination of characteristics: whereas 'WEKpiflaspas' bears very double flowers (about 56 to 118 petals) of soft gold coloration, 'MEIkolyma' bears double flowers of bright red-purple coloration with lesser petalage (about 67 to 70 petals). The new variety bears medium-large sized flowers (about 7.9 to about 10.9 cm. in diameter), whereas the seed parent bears significantly larger flowers (about 13.0 cm. in diameter).

The new variety may be distinguished from its pollen parent, 'WEKjunjuc' by the following combination of characteristics: whereas 'WEKpiflaspas' bears very double flowers (about 56 to 118 petals) of soft gold coloration, 'WEKjunjuc' bears double flowers of sparkling clear yellow coloration with significantly lesser petalage (about 30 to 41 petals). The new variety has a bushy upright somewhat spreading growing habit (about 86 to about 98 cm. in height), whereas the pollen parent has a bushy rounded significantly taller growing habit (about 120 to about 150 cm. in height).

COMPARISON WITH THE CLOSEST COMMERCIALLY AVAILABLE CULTIVAR

The new variety may be distinguished from its closest commercially available cultivar, 'WEKvossutono' (U.S. Plant Pat. No. 18,473) by the following combination of characteristics: whereas 'WEKpiflaspas' bears very double flowers (about 56 to 118 petals) of soft gold coloration, 'WEKvossutono' bears very double flowers of butter gold coloration with significantly lesser petalage (about 30 to 45 petals). The new variety has a bushy upright somewhat spreading growing habit (about 86 to about 98 cm. in height), whereas the closest commercially available cultivar has a compact and bushy significantly shorter growing habit (about 70 to about 85 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

FLOWER

The new variety sometimes bears its flowers singly, sometimes in clusters of two to four per stem. Flowers may be borne in regular rounded clusters on strong moderately short to medium length stems (about 21 to about 44 cm.). The cluster ranges from about 9.5 to about 12.5 cm. in diameter. Outdoors, the plant blooms abundantly and nearly continuously during the growing season. The flowers have a slight tea to somewhat fruity fragrance.

BUD

The peduncle is about 2.0 to about 8.7 cm. in length, of average to somewhat heavy caliper (about 0.2 to about 0.5 cm. in diameter), and usually erect to moderately stiff. It is somewhat rough, with few stipitate glands, and very few hairs and small prickles. Peduncle color is between 146D and 146B usually heavily suffused, sometimes especially on the side exposed to the sun but often all around the peduncle, with between 187B and 187A.

Before the calyx breaks, the bud is about 1.1 to about 2.2 cm. in diameter at the widest point, about 1.3 to about 2.3 cm. in length, and pointed to somewhat ovoid in shape. The surface of the bud bears between 8 to 11 foliaceous appendages with many hairs, usually with slender entire foliaceous parts extending beyond the tip of the bud about 1/4 or more of its length. Bud color is between 137C and 138B often heavily suffused, especially on the side exposed to the sun, with between 187A and 187B.

The sepals are 5 per flower, about 1.8 to about 3.4 cm. in length and about 0.7 to about 1.2 cm. in width at the widest point. The outer surface color of the sepal is between 137C and 138B often heavily suffused, especially on the side exposed to the sun, with between 187A and 187B. The outer surface of the sepal is smooth and bears between 0 to 5 foliaceous appendages with many hairs. The inner surface color of the sepal is near 146D broadly bordered by near 137B. After the sepals open, the inner surface color is sometimes heavily suffused, especially on the area exposed to the sun, with between 187A and 187B. The inner surface of the sepal is covered with fine wooly tomentum; sepal margins are entire and lined with some stipitate glands and many hairs. The sepals are moderately permanent, and usually straight in shape with acute apices.

The receptacle of the flower is of moderately, short to medium length (about 0.2 to about 0.6 cm.) and moderately thin to average in caliper (about 0.5 to about 1.2 cm. in diameter). The receptacle is cup-shaped in form. Its surface is smooth with few hairs and with moderately thick fleshy walls. The receptacle color is between 144A and 146C sometimes heavily suffused, especially on the side exposed to the sun, with between 187A and 187B.

As the petals open (after the calyx breaks), the bud is about 1.7 to about 2.2 cm. in diameter at the widest point, about 2.0 to about 2.7 cm. in length, and moderately ovoid to somewhat pointed in form. The color of the under surfaces of the newly opened petals is between 26C and 26D often heavily suffused on the outermost petals with near 60A to as dark as between 187B and 59A. At the point where the petal attaches, there is a moderately large zone of between 145B and 144D. The color of the upper surfaces of the newly opened petals is between 1D and 154D. At the point where the petal attaches, there is a somewhat small zone of between 150B and 151D.

BLOOM

When fully open, the bloom ranges from about 7.9 to about 10.9 cm. in diameter. Petalage is very double with about 56 to 118 petals and about 6 to 25 petaloids irregularly arranged. When partially open, the bloom form is somewhat globular to cupped, and the petals are tightly spiraled to cupped to somewhat undulated with petal edges somewhat reflexed outward. When fully open, the bloom form is somewhat cupped to slightly flat, and the petals are loosely cupped to moderately undulated with petal edges somewhat reflexed outward. Sometimes some of the intermediate and inner petals are folded along the midrib.

PETALS

The substance of the petals is moderately heavy and of somewhat thin to medium thickness, with upper surfaces somewhat satiny and under surfaces slightly shiny. The petals are about 2.3 to about 4.2 cm. in length and about 1.6 to about 4.2 cm. in width at the widest point. Petal margins are entire.

The outer petals are moderately obovate to somewhat rounded in shape with rounded to sometimes somewhat mucronate apices.

The inner petals are broadly oblanceolate in shape with rounded apices.

Petaloids are about 0.5 to about 3.2 cm. in length and about 0.4 to about 1.9 cm. in width at the widest point. Petaloids are irregularly shaped moderately oblanceolate to somewhat subulate with rounded apices.

NEWLY OPENED FLOWER

The under-surface color of the outer, intermediate and inner petals is between 25D and 24B. At the point where the petal attaches, there is a moderately small zone of between 1D and 154D. The upper surface color of the outer, intermediate and inner petals is between 15D and 14D. There is no visible change in coloration at the point where the petal attaches.

The under and upper surface colors of the petaloids are similar in coloration to the upper and under surfaces of the intermediate and inner petals.

The general tonality of the newly opened flower is between 15D and 14D.

THREE-DAY-OLD FLOWER

The under-surface color of the outer, intermediate and inner petals is between 19B and 18B. At the point where the petal attaches, there is a moderately small zone of near 5C. The upper surface color of the outer, intermediate and inner petals is between 11B and 18C. There is no visible change in coloration at the point where the petal attaches.

The under and upper surface colors of the petaloids are similar in coloration to, the upper and under surfaces of the intermediate and inner petals.

The general tonality of the three-day-old flower is between 11B and 18C.

On the spent bloom, the petals usually drop off cleanly.

In November in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 150) and are arranged regularly about the pistils; a few are mixed with petaloids. The filaments are of medium to somewhat long length (about 0.5 to about 1.0 cm.) most with anthers. Filaments are between 5A and 6A in color. The anthers are moderately small for the class and all open approximately at the same time. Anther color when immature is near 20A on the external part and near 11D on the internal part. Anther color at maturity is near 163B on the external part and near 200B on the internal part. Pollen is moderate and between 20B and 21D in color.

FEMALE REPRODUCTIVE ORGANS

Pistils vary in number (average about 135). The styles are moderately even, somewhat short to average in length (about 0.3 to about 0.7 cm.), thin in caliper, and loosely bunched to somewhat separated. Stigma color is between 17D and 16C. Style color is between 1D and 154D usually heavily suffused with between 60A and 60B. Ovaries are usually all enclosed in the calyx. The ovaries are of somewhat large size and between 158B and 158C in color.

Hips have not been observed on this variety when grown in Wasco, Calif.

FOLIAGE

The compound leaves are usually comprised of three to seven leaflets and are borne abundantly. The seven-leaflet leaves are about 10.1 to about 15.7 cm. in length and about 6.8 to about 11.2 cm. in width at the widest point, moderately leathery to somewhat crisp in texture on both sides, and glossy in finish on the upper side and matte to somewhat semi-glossy in finish on the underside. The leaves have a pinnate venation pattern. The terminal leaflets are about 4.4 to about 7.5 cm. in length and about 2.5 to about 4.7 cm. in width at the widest point, shaped moderately ovate with acute apices and rounded bases. Their margins are usually simply serrate.

The upper surface color of the mature leaf is between 137A and 147A. The under-surface color of the mature leaf is between 148B and 147B. The under and upper colors of the leaf veins on the mature leaf are similar in coloration to the upper and under surfaces colors of the mature leaf. The upper surface color of the young leaf is between 147A and 146A, usually heavily suffused with between 187B and 187A. The under-surface color of the young leaf is between 138B and 139C, usually heavily suffused with between 187B and 187A. The under and upper colors of the leaf veins on the young leaf are similar in coloration to the upper and under surfaces colors of the young leaf.

The rachis is about 4.4 to about 7.2 cm. in length, about 0.1 to about 0.15 cm in width at the widest point, and rough. The upper side is deeply grooved with few hairs and stipitate glands on the edges of the grooves. The under side of the rachis is rough with few stipitate glands and small prickles. The rachis color is near 145C on the under side and near 146B on the upper side, usually heavily suffused on the young leaves with between 187B and 187A.

The stipules are about 1.0 to about 1.8 cm. in length and of medium to somewhat wide width (about 0.4 to about 0.7 cm.) with medium length straight points that usually turn out at an angle of more than 45 degrees and sometimes recurve toward the stem. The under and upper surface color of the stipule is near 138A often heavily suffused on the young leaves with between 187B and 187A. The upper and under surfaces of the stipules are smooth in texture.

The petiole is moderately light in caliper and rough. The upper side is deeply grooved with few hairs and stipitate glands on the edges of the grooves. The under side of the petiole is rough with few stipitate glands and small prickles. The petiole is about 0.4 to about 1.1 cm. in length and about 0.1 to about 0.15 cm in width at the widest point. The petiole color is near 145C on the underside and near 146B on the upper side, usually heavily suffused on the young leaves with between 187B and 187A.

The plant displays an above average degree of resistance to powdery mildew (*Sphaerotheca pannosa*), downy mildew (*Peronospora sparsa*) and rust (*Phragmidium* sp.) and an average degree of resistance to black spot (*Diplocarpon rosae*) as compared to other commercial varieties grown under comparable conditions in Wasco, Calif. The plant's winter hardiness and drought/heat tolerance are yet to be determined.

GROWTH

The plant has a bushy upright somewhat spreading medium height growing habit (about 86 to about 98 cm. in height and about 72 to about 84 cm. spread at the widest point), with full branching. It displays moderately vigorous growth and the canes are of medium to somewhat heavy caliper for the class (about 1.2 to about 1.5 cm. in diameter at the widest point).

The color of the major stems is between 146A and 146C. The major stems are rough in texture and they bear many large prickles that are about 0.7 to about 1.3 cm. in length. The large prickles are angled slightly downward with a moderately long broad oval base; prickle color is between 166A and 177A. The major stem bears some small prickles of similar shape and coloration.

The color of the branches is between 137C and 146A sometimes moderately suffused with between 187A and 187B. The branches are rough in texture and they bear some large prickles which are of similar size and shape to the large prickles on the major stems; prickle color is between 146D and 152D often moderately suffused with between 187A and 187B. The branches bear few small prickles of similar shape and coloration.

The color of the new shoots is between 146C and 138B usually heavily suffused with between 187B and 187A. The new shoots are rough in texture and they bear some large prickles which are of similar size and shape to the large prickles on the major stems; prickle color is between 146D and 152D often heavily suffused with between 187A and 187B. The shoots bear few small prickles of similar shape and coloration.

I claim:

1. A new and distinct Floribunda rose plant of the variety designated 'WEKpiflaspas' substantially as described and illustrated herein.

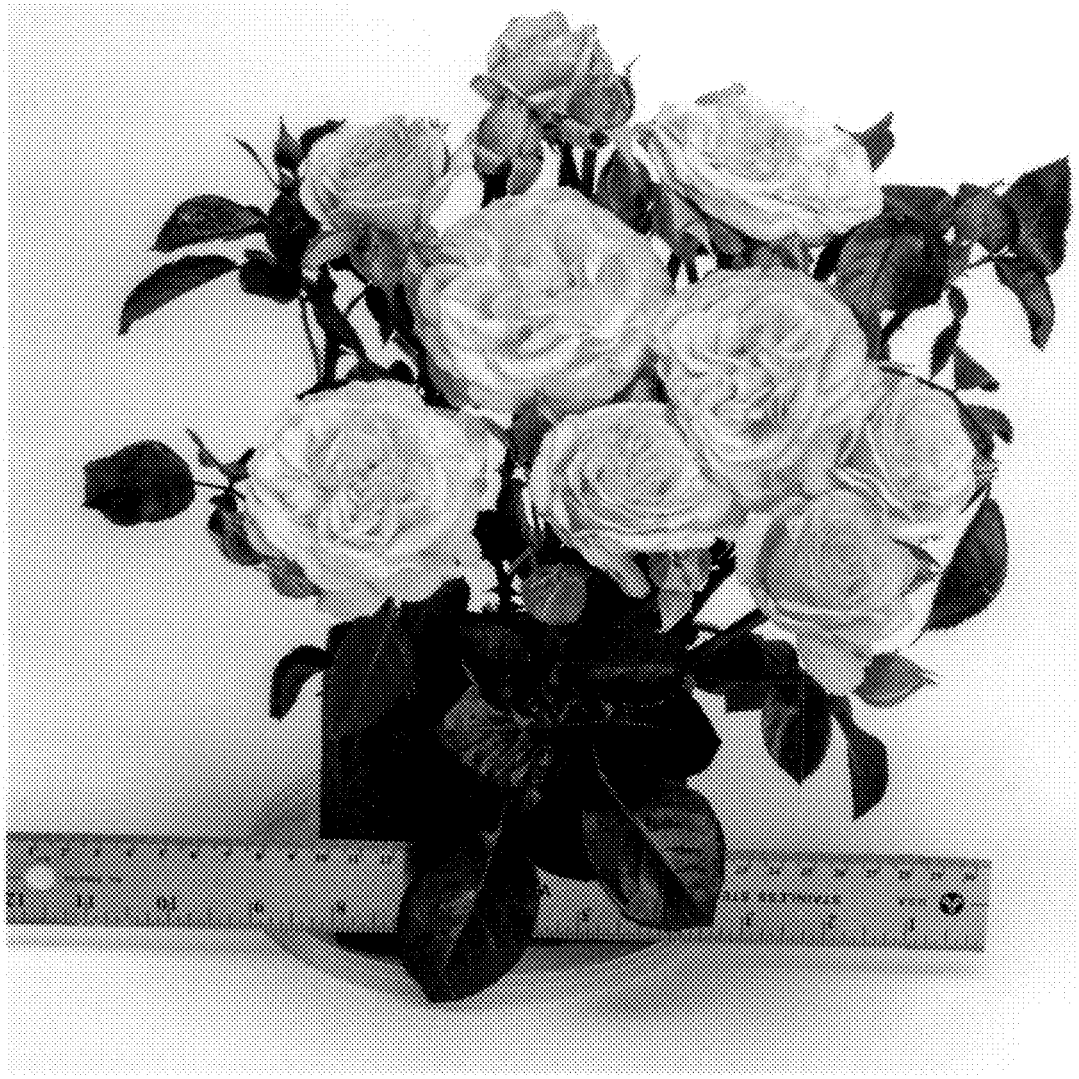

* * * * *